(12) United States Patent
Pănculescu (10) Patent No.: US 8,268,253 B2
(45) Date of Patent: Sep. 18, 2012

(54) AIR PURIFIER

(75) Inventor: Dumitru Pănculescu, Ploiesti (RO)

(73) Assignee: Horatiu Sorin Terpe, College Point, NY (US)

( * ) Notice: Subject to any disclaimer, the term of this patent is extended or adjusted under 35 U.S.C. 154(b) by 519 days.

(21) Appl. No.: 12/426,718

(22) Filed: Apr. 20, 2009

(65) Prior Publication Data

US 2010/0135863 A1    Jun. 3, 2010

(30) Foreign Application Priority Data

Apr. 21, 2008  (RO) .............................. A2008/00311

(51) Int. Cl.
*A62B 7/08* (2006.01)
*A61L 9/00* (2006.01)
*B03C 3/40* (2006.01)

(52) U.S. Cl. ................ 422/121; 422/120; 422/5; 96/83; 96/84

(58) Field of Classification Search .................. 219/780, 219/88, 124.33; 422/5, 120, 121, 780, 88; 95/57, 81, 73, 74; 96/15, 18, 25, 54, 55, 96/75, 76, 77, 78, 79, 83, 84, 99, 100
See application file for complete search history.

(56) References Cited

U.S. PATENT DOCUMENTS

| | | | |
|---|---|---|---|
| 4,643,745 A | 2/1987 | Sakakibara et al. | |
| 5,055,115 A * | 10/1991 | Yikai et al. | 96/59 |
| 5,456,741 A * | 10/1995 | Takahara et al. | 96/22 |
| 6,193,788 B1 | 2/2001 | Nojima | |
| 6,368,692 B1 | 4/2002 | Yamazaki et al. | |
| 6,652,816 B2 * | 11/2003 | Hwang | 422/186.07 |
| 6,735,830 B1 * | 5/2004 | Merciel | 250/324 |
| 7,595,030 B2 * | 9/2009 | Joannou | 422/186.04 |
| 7,771,671 B2 * | 8/2010 | Taylor et al. | 422/186.04 |

FOREIGN PATENT DOCUMENTS

| | | |
|---|---|---|
| DE | 909982 | 4/1954 |
| EP | 0862949 | 5/1998 |
| EP | 1058066 | 6/2000 |
| WO | 2007/040416 | 4/2007 |

* cited by examiner

*Primary Examiner* — Regina M. Yoo

(74) *Attorney, Agent, or Firm* — Hershkovitz & Associates LLC; Abe Hershkovitz (57) ABSTRACT

An air sterilizer that operates by electro-kinetic conversion of energy is provided. The sterilizer can have an electro-kinetic converter, rows of needles fastened along support plates, and neutralizing electrodes. The converter can have a rectangular frame with two armatures joined by electrically insulating transverse plates. The armatures can be provided on one of the margins with a row of rectangular notches, equally-spaced with a constant pitch. In the notches, the ion-generating electrodes can be introduced. On their opposed margin, the plates can be interleaved at the same pitch and with V-shaped openings where the neutralizing electrodes can be introduced. The electrodes can be affixed by insulating covers, in the shape of the letter U. Each cover can be elastically deformable. The power supply can derive from an impulse generator with sufficient voltage to form an intense electric field which can ionize surrounding air and create a plasma zone.

17 Claims, 4 Drawing Sheets

_AIR PURIFIER_

CROSS-REFERENCE TO RELATED APPLICATIONS

This application claims priority to Romanian Patent Application Number a 2008/00311 filed on Apr. 21, 2008, the disclosure of which is hereby incorporated by reference in its entirety.

BACKGROUND OF THE INVENTION

1. Field of the Invention

The present invention relates to an air cleaner, more particularly, an air sterilizer that performs electro-kinetic conversion of energy without mechanical devices in movement.

2. Discussion of Background Information

Previous to this invention, an air sterilizer was known (U.S. Pat. No. 4,643,745), wherein the air is moved by the conversion of the electric energy into kinetic energy without mechanical devices in movement. This apparatus contains two parallel metal armatures with the function of electrodes, each armature being supplied with a certain direct current (DC) voltage. The armatures are provided with openings that allow air circulation through and between them. One of the armatures is provided with sharp needles located perpendicular to the armature plane and oriented towards the second armature. These needles constitute discharging electrodes, and the second armature is an oppositely charged electrode (i.e., neutralizing electrode). A third armature, which is considered as an intermediary, is connected to the ground and is located between the first and second armatures. The location of the two extreme armatures and the supply of DC voltage is made so that, in the region of the points of the needles, there occurs a stable corona discharge by which ions are produced. The created ions move in the electric field region toward the neutralizing electrode, and in their movement they entrain individual molecules, groups of molecules and other neutral particles, thereby determining the air movement between the two armatures. Some of the neutral particles, such as dust, also are partially ionized in the electric field, and are attracted by the neutralizing electrode, which collects them. Thus, as long as the electric field and corona discharge are maintained, the air is recirculated and purified at the same time. The third electrode allows for an increase of the air velocity without significant extra ozone being generated.

However, with the above-described apparatus, certain disadvantages exist. For example, it is relatively complex, expensive to construct, and requires two high voltage sources and three distinct armatures. Additionally, once a discharge takes place between the electrodes, that discharge does not stop. This is in contrast to the present invention. Due to the manner in which the two impulses are controlled, the discharge will remain only in the proximity of the first electrode.

There also is known another apparatus for cleaning the air (International Patent Application PCT/RO2005/000014) by the inventor of the present invention. This apparatus comprises an electro-kinetic converter which includes two armatures having the role of electrodes, wherein a discontinuous polarized electric field is produced for a few microseconds in duration. In this apparatus, an electric field is created based on the difference of potential between the electrode voltage to which the negative potential (point-type electrodes) is applied and the potential of the atmospheric mass between the two armatures. An electric field then is created based on the difference of potential between the potential of the atmospheric mass extant between the two armatures and the voltage of the electrode to which the positive potential (frame-type electrodes) is applied, so that the created electric field, which has the same direction and is apparently continuous in action, is formed of consecutive voltages for a few microseconds in duration between the moments of their occurrence, having no simultaneous action.

Thus, a high intensity electric field is formed between the two armatures. One of the armatures comprises a metal panel provided with a row of sharp-pointed metal rods welded perpendicular to the surface of the panel and directed toward the second armature. The second armature has the shape of a metal frame surrounding, and at some distance from, the row of points of the metal rods. Both armatures are secured to an insulating base, as there are applied between them high voltage impulses generated by an electric power source. Ions are generated in the high intensity electric field created around the sharp rod points.

This solution is relatively simple and efficient but also is rather fragile, resulting in damage during the transportation and operation of the apparatus, and it is significantly difficult to replace damaged elements of the converter.

SUMMARY OF THE INVENTION

The technical problem solved by the present invention is the creation of an improved variant of an air sterilizer which is reliable and highly efficient, and at the same time has the possibility of operating in various working conditions with various air circulation velocities.

The air sterilizer according to the present invention eliminates the above-mentioned disadvantages and solves the proposed technical problem in that it comprises an electro-kinetic converter including, as an ion-generating electrode, one or more rows of needles secured to one or more supporting plates, and as a neutralizing electrode, lamellar plates (instead of the metal frames, panels can be used), and both electrodes can be supplied with energy from a very high voltage power source, such as an impulse voltage generator. The converter can comprise a rectangular frame having an upper plate and a lower plate joined at the ends thereof by electrically insulating transverse plates. The upper and the lower plates can be provided on one of their margins with a row of constant-pitch, equally-spaced rectangularly-shaped notches into which the ion-generating electrodes can be introduced and, on the margin opposed to the notches, these plates can be provided with interleaved, outwardly-opening V-shaped cut-outs having the same pitch as the notches, into which cut-outs the neutralizing electrodes can be introduced. These electrodes can be secured in position by the use of insulating covers having substantially U-shaped profiles, and the covers can be introduced by elastic deformation onto the upper and lower plates. The electric power supply can be an impulse voltage generator (FIT) which generates and applies sufficiently high voltage impulses so as to determine the formation of, in the region of the points of the needles, a structured, high-intensity electric field capable of producing an ionizing process and a plasma zone. The generator of high voltage impulses (FIT) can have a network filter and an alternating current (AC) frequency impulse converter which can provide stabilized DC voltages to the functional units of the generator. The functional units of the generator can be a control unit, an impulse oscillating and shaper unit, a fast commutation shaper unit, and a power amplifier supplying a voltage step up whose secondary winding is connected to two rectifiers, which can supply the two armatures of the electro-kinetic converter.

By using the air sterilizer according to the present invention, the following advantages are obtained. There is an increased flow rate and velocity of the handled air stream, as well as in the volume of ions and the formed ozone, while consuming less power (less than 20 w). At the same time, these flow rates and volumes, respectively, can be varied by manual controls depending on the desired use of the air sterilizer. For example, the flow rates can be varied based on the volume/size of the room where the apparatus is installed, or on the degree of air pollution in the room. Additionally, the electro-kinetic converter can be reliable and can be very easily dismounted, repaired and/or reassembled, if necessary. Furthermore, the very high voltage impulse generator that is part of the air sterilizer is reliable and can be operated in a wide variety of working conditions and, if necessary, any of its units can be easily replaced.

Therefore, according to one aspect of the present invention, an air sterilizer comprises an electro-kinetic converter having an ion-generating electrode. The ion-generating electrode can comprise at least one row of needles secured on at least one support plate, two or more lamellar plates, two or more U-shaped elastically deformable insulating covers, and a very high voltage power source. The lamellar plates can serve as neutralizing electrodes. The electro-kinetic converter also can comprise a rectangular frame having an upper plate and a lower plate, and two or more electrically-insulating transverse plates. The upper and lower plates of the rectangular frame can be joined at their ends by the electrically-insulating transverse plates. The upper and lower plates can have margins, and on one of the margins of the upper plate or the lower plate can be a row of constant-pitch, equally-spaced rectangular notches. The ion-generating electrode can be introduced through the rectangular notches, and on a margin opposed to the ion-generating electrode can be two or more outwardly-facing V-shaped openings which are interleaved and at the same pitch. Finally, the neutralizing electrodes can be introduced through the V-shaped openings, and can be secured in place on the upper plate and the lower plate by the U-shaped elastically-deformable insulating covers.

Furthermore, the ion-generating electrode can comprise a metal support blade and at least one row of needles. The at least one row of needles can be fastened lengthwise and at a well-determined pitch along the metal support blade, the needles being parallel to one another and perpendicular to the blade. The neutralizing electrodes can be made of two or more elements of metal strip, profiled lengthwise in a V shape and having equal arms that open at an angle of from 60 degrees to 120 degrees.

Furthermore, the points of the rows of needles of the ion-generating electrode can be arranged along a straight line and parallel to each edge of the neutralizing electrodes and equally-spaced therefrom.

Furthermore, the needles can be made out of wire comprising stainless steel alloyed with titanium, and the needles can have a diameter from 0.8 mm to 1.0 mm, and a length from 10 mm to 15 mm, and the points of the needles are very sharp so that a ratio of the length of the point to the diameter of the needle is 5 to 10. The minimum values of the ratio can be selected based on supplying the converter with a lower voltage of 10 kV, and the maximum values, for values higher than 10 kV, The needles can be spaced at a pitch from 1 mm to 5 mm on the support blade.

The electric power source can be an impulse voltage generator which generates very high voltage, and applies consecutive negative and positive impulses between the upper and lower plates which function as the electrodes. The negative and positive impulses can have sufficiently high voltage so as to form an electric field in the region of the points of the needles. The electric field can be of a sufficient intensity to create a ionization process and a plasma zone.

In one or more embodiments, the points of the rows of needles of the ion-generating electrode can be arranged along a straight line and parallel to each edge of the neutralizing electrodes, and equally spaced therefrom.

Furthermore, the oscillating and impulse shaper unit can comprise at least one of, an oscillator with an operational amplifier, an oscillator output signal, or an oscillator input shaper. The oscillator with an operational amplifier can generate saw-toothed waveforms, and the frequency and the duration of the ramps and drops of the saw-tooth waveforms can be adjusted using a potentiometer. The oscillator output signal can be connected to, and processed by, the oscillator input shaper. The oscillator input shaper can comprise six serially-connected logic reversers which generate rectangular impulses with adjustable pulse duty factor.

Furthermore, the very high voltage impulse generator can comprise a network filter and an AC/DC frequency converter. The AC/DC frequency converter can supply stabilized DC voltages. The stabilized DC voltages can provide power to functional units of the generator, and the functional units of the generator can comprise at least one of, a control unit, an oscillating and impulse shaper unit, a rapid commutation shaper unit, or a power amplifier. The power amplifier can supply a voltage step up whose secondary winding can be connected to two rectifiers supplying the upper plate and lower plate of the electro-kinetic converter.

Furthermore, the AC/DC frequency converter together with the network filter can carry out a separation of nulls by creating a virtual null for other units of the high frequency impulse generator. The virtual null can be different from a null of the supply network.

Furthermore, the rapid commutation shaper unit can receive impulses generated by the oscillating shaper unit through an optocoupler. The optocoupler can comprise at least one of, a reverser unit or a repeating unit. The reverser unit and the repeating unit can comprise power commutation transistors at an output of the rapid commutation shaper unit, resulting in positive rectangular impulses with very rapid drops. The very rapid drops can be applied to an input of a power amplifier unit. The power amplifier can supply a voltage step up.

Furthermore, the impulses resulting in the secondary winding of a transformer can comprise a negative impulse followed by a positive impulse for each positive impulse applied to an input of a power amplifying unit. The positive impulse and the negative impulse can be rectified by a first rectifier and a second rectifier. The first rectifier and second rectifier can comprise at least two serially-connected rectifying diodes. The first rectifier can allow only negative impulses to supply an ion generator. The second rectifier can allow only positive impulses to supply the neutralizing electrodes.

Still according to one or more embodiments, the air sterilizer can comprise an optocoupler controlling the passing of impulses from an oscillating shaping unit to a rapid commutation shaper unit. The optocoupler can be controlled by signals transmitted by a control unit, allowing a working mode to be selected from three possible working modes. The three possible working modes can have a predefined duration in which the optocoupler can be activated and a duration in which it is deactivated. The control unit can have a push button interface, allowing a user to select one of the three possible working modes, and a lagging signal generator to generate a corresponding lagging signal for each working mode.

Furthermore, the first of the three possible working modes can comprise an optocoupler which can be continuously activated, allowing a very high frequency generator to continuously supply impulses to the upper plate and lower plate of the electro-kinetic converter. The second of the three possible working modes can comprise an optocoupler which can be intermittently activated, allowing for a three second active period alternating with a three second inactive period, and during the inactive period, impulses cannot pass through to the optocoupler. The third of the three possible working modes can comprise an optocoupler in which the active period can be three seconds and the inactive period can be eighteen seconds.

Other exemplary embodiments and advantages of the present invention may be ascertained by reviewing the present disclosure and the accompanying drawings.

BRIEF DESCRIPTION OF THE DRAWINGS

This invention is further described in the detailed description which follows, with reference to the noted plurality of drawings by way of non-limiting examples of embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in order to provide what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

According to one or more embodiments of the present invention, the air sterilizer can comprise an electro-kinetic converter A having several electro-kinetic cells that can be identical in respect to construction and functionality, as they are described hereinafter. The respective electro-kinetic cells can be connected in parallel and supplied with very high voltage by an impulse voltage generator.

Figure 1:
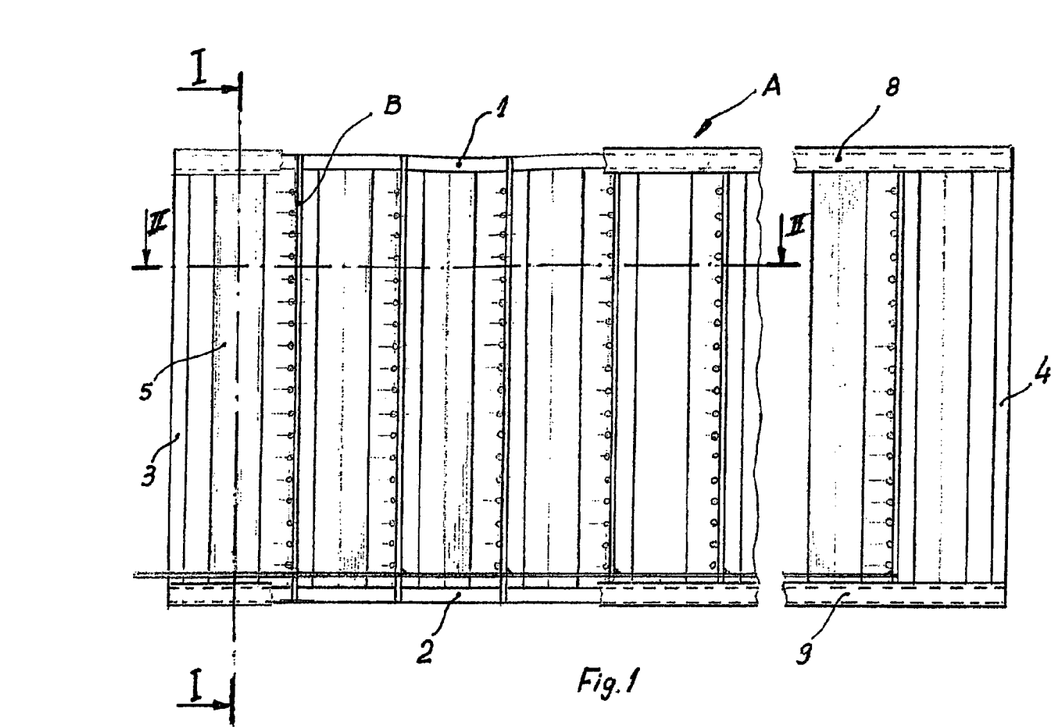
FIG. 1 is a rear view of the electro-kinetic converter according to one or more embodiments of this invention.
Figure 2:
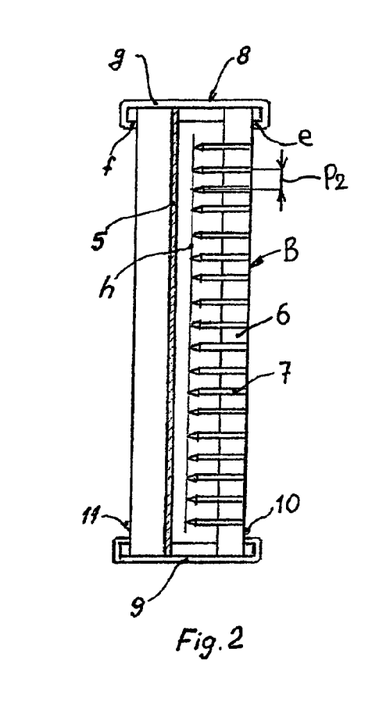
FIG. 2 is a cross-sectional view taken along line I-I in FIG. 1.
Figure 3:
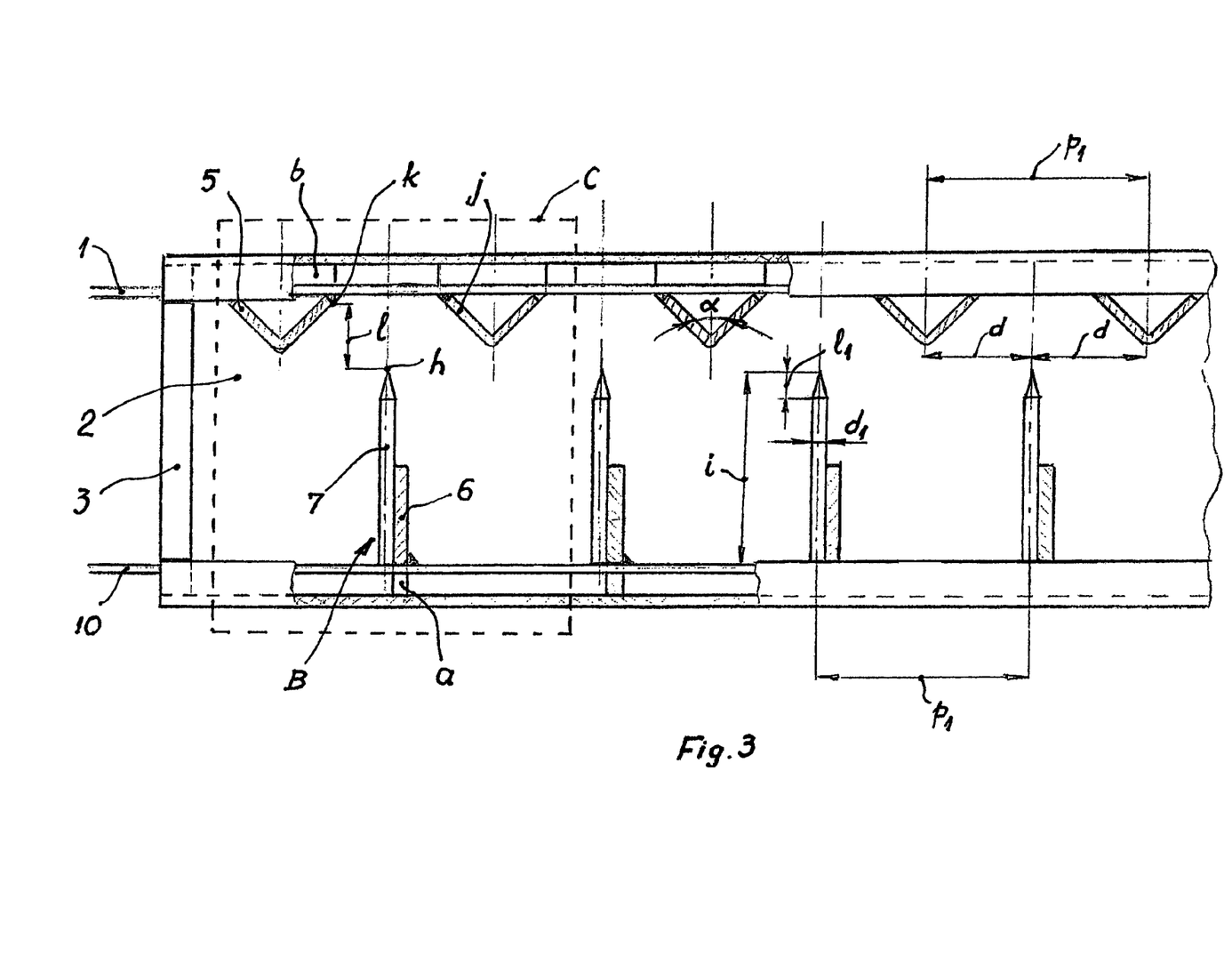
FIG. 3 is a longitudinal plan view taken along line II-II in FIG. 1.
Figure 4:
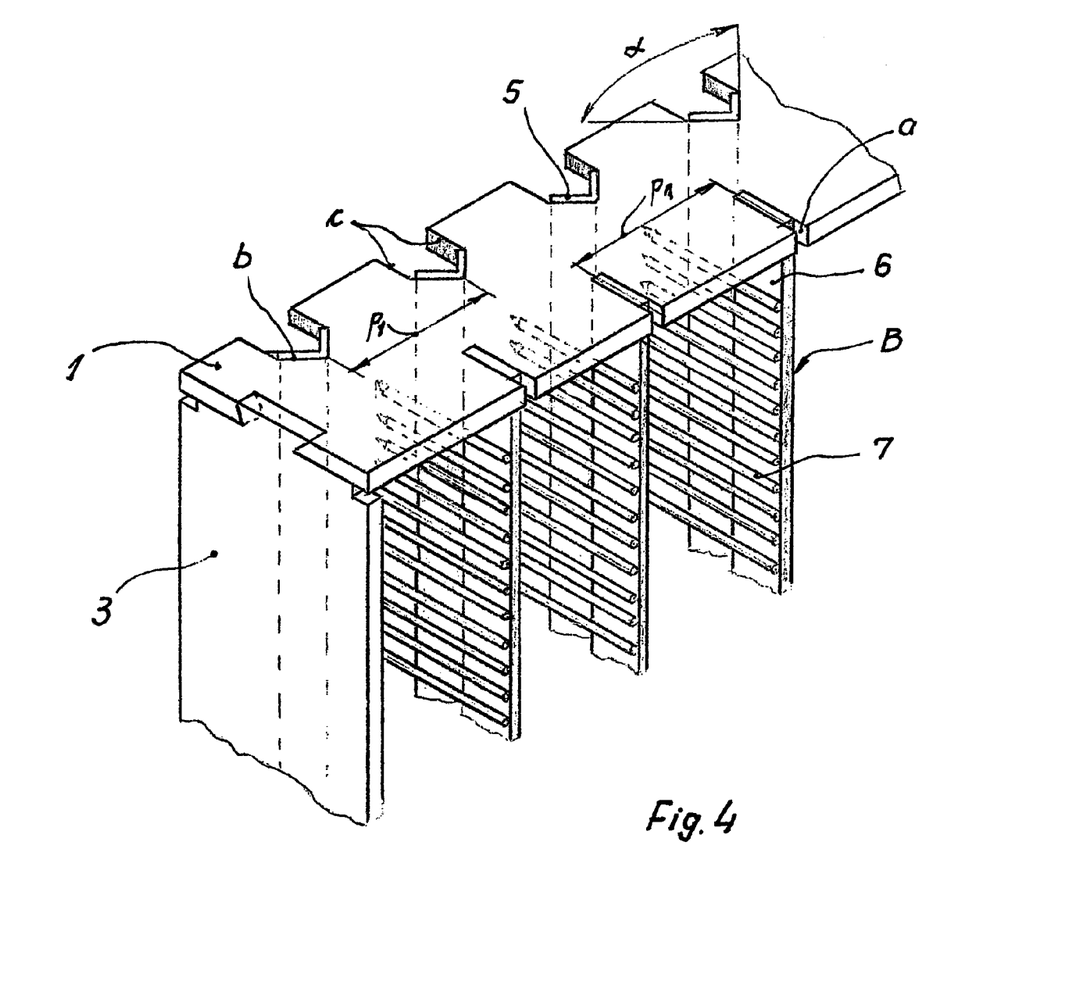
FIG. 4 is an elevational view of the electro-kinetic converter of FIG. 1 without the upper cover.

The electro-kinetic converter A in FIGS. 1 to 4 can have a geometrical shape of a parallelepiped or it can have a cuboid (rectangular) frame comprising an upper plate 1 and a lower plate 2 joined at their respective ends by two transverse plates 3 and 4. When joined, the upper plate and the lower plate can form an angle of ninety degrees with the adjacent transverse plates. Joining upper and lower plates 1, 2 to transverse plates 3,4 can be achieved, for example, using screws, a dovetail system, a suitable adhesive, etc. Elements 1 through 4 can be created using an electrically-insulating material. The above-described construction is represented in FIG. 4.

Upper plate 1 and lower plate 2 can be identical in shape, details and dimensions. In addition, the upper and lower plates, as shown in FIGS. 3 and 4, can be provided on one of their margins with a row of rectangularly-shaped notches a. On the side opposite the row of rectangularly-shaped notches a, there can be a row of V-shaped openings b, with each V-shaped opening having two parallel and transverse flanks c. The rectangularly-shaped notches a and the V-shaped openings b can be provided at a constant pitch $p_1$, which can be the same for notches a and openings b.

As can be seen in FIG. 3, through each of the notches a of the upper plate 1 and of the lower plate 2, one end of an armature B (also called an ion generator) can be introduced which contains the discharging electrodes. Into each of the openings b, the ends of one profiled element 5 can be introduced, which can form the other ion generator which is an oppositely charged electrode (also called a neutralizing electrode) to that of the converter. The neutralizing electrode 5 can be profiled as a V-shaped equal-armed element, as shown in FIGS. 3 and 4.

FIG. 2 depicts an ion generator B, including a metal support blade 6 having needles 7 that are spaced at a well-determined pitch $p_2$. The needles can be fastened to blade 6 by, for example, welding, adhering or any other suitable process. The needles comprise the discharging electrodes of the ion generator B. Fastening of the metal support blade together with the needles allows for continuous electrical contact (e.g., conductance) between the blade 6 and the needles 7. The needles can be arranged in a row lengthwise and parallel to one another on the support blade 6 and arranged lengthwise in the plane of the blade. The position of the notches a on the upper plate 1 and the lower plate 2 can be selected so that a plane can be formed by the axis of each row of needles 7. Each blade 6 of ion generator B can be arranged parallel to the planes of the neutralizing electrodes 5. Each of the neutralizing electrodes can be placed on either side of the ion generator B and can be equally spaced from elements 5 at a distance of $d=p_1/2$ (see FIG. 3). The ion generators B and the neutralizing electrodes 5 can be in a fixed position in their seats on the upper plate 1 and lower plate 2 by using two covers, an upper cover 8 and a lower cover 9. The upper cover 8 and lower cover 9 can be identical in both shape and in dimension, as well as comprise elastically deformable insulating material which can be expanded. Each cover can be introduced onto the upper plate 1 and lower plate 2 by expanding the elastically deformable insulating material. As shown in FIG. 2, the covers can be made of an extruded profile in a suitable plastic material that can be in the general shape of the letter U. FIG. 2 depicts a cross-sectional profile where the wings e and f flare towards the inside of a central part g (the bottom of the U). It can easily be seen that this construction allows for the rapid and safe mounting and dismounting of the whole converter assembly.

In viewing FIG. 2, it also can be seen that the points of each row of needles 7 can be arranged along a straight line h, which can be parallel to each edge of the neighboring discharging electrode 5. These rows of needles can preferably comprise wire of stainless steel alloyed with titanium having a diameter of from 0.8 mm to 1.0 mm and a length of from 10 mm to 15 mm. The points on the needles 7 can be sharpened to form a ratio of 5 to 10 (i.e., 1 to 2) when comparing the length $l_1$ of the points to the diameter $d_1$ of the needle, respectively. The minimum values of the $l_1/d_1$ ratio can be selected when the converter is supplied with a voltage lower than 10 kV. The maximum values can be selected when the converter is supplied with a voltage exceeding 10 kV. The needles 7 can be located on the support blade 6 at a pitch of from 1 mm to 5 mm.

The neutralizing electrodes 5 can comprise a metal such as aluminium or steel. The neutralizing electrodes can be in the shape of the letter V so that, between the two wings j of each profiled element, an angle of from 60 degrees to 120 degrees is formed. The value of the angle α can also be selected based on the density of the ion generating subassemblies B, namely the size of the pitch $p_1$. At the lower values of the pitch $p_1$, the low value of the angle α can be adopted. Between the straight line h, along which the points of needles 7 are inscribed, and the edges k of the neutralizing electrodes, the distance l can have an optimum length of from 10 mm to 16 mm, and preferably 12 mm.

The ion generator B and the wings of the two left end and right end adjoining neutralizing electrodes 5 can form an electro-kinetic cell C which is indicated by the dotted line in FIG. 3. It can be considered that the converter A comprises a succession of such identical cells (as depicted in FIG. 3), which are easy to make and assemble.

The voltage supply of the armatures of the converter can be made by utilizing conductors 10 and 11, respectively, the first of them being affixed to each support blade 6 and the second conductor can be affixed to the edge of each neutralizing profiled element 5. More precisely, the ion generators B and the neutralizing electrodes 5 can be connected to the negative pole and the positive pole, respectively, of a very high voltage power supply. The converter operation is relatively simple.

Thus, in the region of the points of the needles, the electric field can become very intense, which can lead to the ionization of the surrounding air and the formation of a plasma zone. Consequently, the shape and diameter of the needles, and the distance between them can be among the parameters that determine performance. Therefore, the points can be selected to ensure reliability and optimum ionization properties for optimum performance. Thus, it is preferable that the points of the needles be as sharp as possible to ensure better electron injection. Additionally, the needle diameter should not be less than a minimum value, which serves to prevent the rapid melting of the point, for example, during the aforementioned process. It also is very important that the needles be uniform, because any imperfection or non-uniformity in the shape or resistivity of a needle can lead to an imperfect or non-uniform electrical field. This less than optimal field can be undesirable and lead to a breakdown of the field, for example.

The electric power supply can comprise very high voltage, such as an impulse voltage generator FIT, which generates and applies, between the two armatures, consecutive negative and positive impulses to the converter armatures. These impulses can be of a sufficiently high voltage to cause the air to ionize in the region of the points of the needles. In this region, the electric field intensity can be very high and cause the generation of electrons and ions, and can cause the creation of a plasma zone. The ions generated in the region of the points can be displaced in the electric field resulting from electrostatic forces, and in their movement, they can hit neutral molecules and particles. When these moving ions hit molecules or particles, they can transfer a part of their kinetic energy by collision and entrain those respective molecules or particles in movement toward the neutralizing electrode. Such movement can be in the direction of the oppositely charged electrode, thereby causing the displacement of the gas mass from the points of the needles 7 towards the planes of these oppositely charged electrodes 5. At the same time, in the region with the moving ions, some of the impure particles, such as dust, smoke and other groups of molecules, also can be ionized by collision with the moving ions, and they can be attracted towards the neutralizing armature where they can be collected. The micro-organisms and other organic impurities also can be destroyed by burning in the cold plasma.

Thus, the air in the region of the electric field between the two electrodes, on the one hand, can be purified by the above-described effect, and on the other hand, can be entrained in a movement in the direction of the points of the needles, thereby allowing air recirculation in a space and air purification in that same space.

The source of the required very high voltage electrical power for this process can be an impulse voltage generator FIT, which can generate and apply, between the two electrodes, consecutive high voltage negative and positive impulses having frequencies outside the audio frequency range, preferably above the range of from 22 kHz and 25 kHz.

The high voltage generator FIT (high or very high voltage) (FIG. 5) can comprise a network filter FR, followed by an AC/DC frequency (impulse) converter CF, which can supply a stabilized voltage source ST. The stabilized voltage source can provide stabilized DC voltages to the other units, such as the control unit BC, oscillating and impulse shaper unit OF, followed by a rapid commutation shaper unit BFR, and a power amplifier AP. The power amplifier can supply a voltage step up Tr whose secondary winding is connected to two rectifiers that supply the two armatures or electrodes B and 5, respectively, of the above-described electro-kinetic converter.

Figure 5:
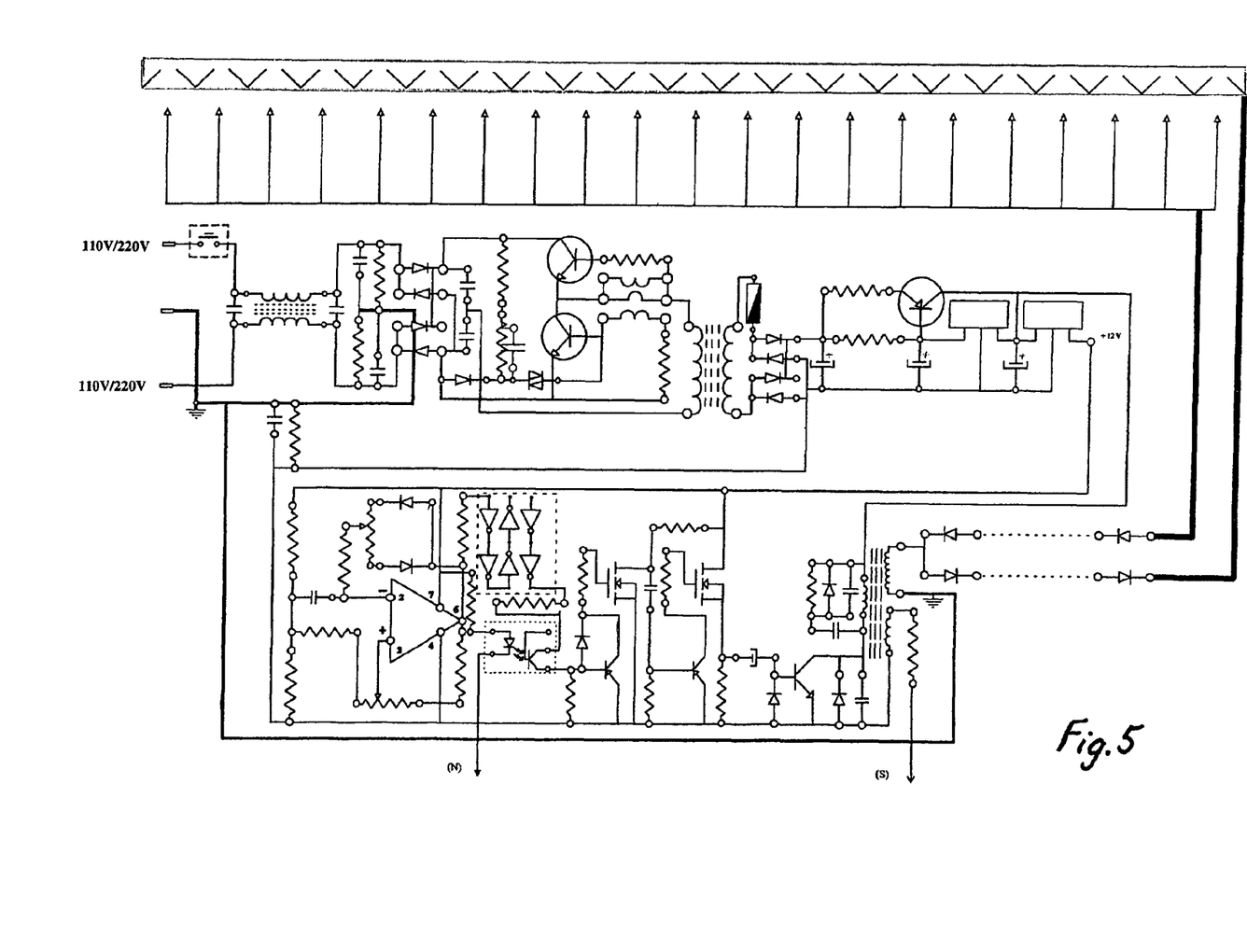
FIG. 5 is an electrical diagram of the impulse voltage generator according to one or more embodiments of this invention.

The network filter FR is a low-pass passive filter which can eliminate the frequencies exceeding 300 Hz as well as random disturbing signals. The network filter also can supply the filtered output voltage to the frequency converter CF.

The frequency converter CF can convert the network frequency into a frequency in the order of from 50 kHz to 2000 kHz by allowing DC voltage to pass through. The converter can comprise a rectifier having an oscillator which generates an intermediary frequency and supplies a transformer through which the voltage source ST can be supplied. The frequency converter CF can work in coordination with the network filter FR to achieve, at the same time, a separation of the nulls by creating a virtual null for the other units of the impulse generator. The virtual null can be different from the supply network null.

The DC source ST can supply the DC voltages for all of the units of the impulse generator FIT. The DC source comprises a rectifier which rectifies the voltage received from the frequency converter CF and can supply (at the output) a non-stabilized and rectified 24V voltage to two voltage stabilizers. The two voltage stabilizers can supply 12V and 24V stabilized voltages to the other units of the impulse generator FIT.

The oscillating and impulse shaper unit OF can comprise an oscillator with type 741 operational amplifier which can generate saw-toothed waveforms with a frequency of about 25 kHz. The oscillator can have the capability of adjusting the frequency, through a potentiometer OFp1, and the duration of the saw-tooth ramp and drop through a second potentiometer OFp2. The oscillator output can be connected to the input of an impulse shaper having six serially-connected logic reversers at the shaper output. This connection can result in rectangular impulses with an adjustable pulse duty factor. The adjustment of the rising gradient and the falling gradient durations can be made by manipulating the second potentiometer OFp2. The impulses at the output of the oscillating unit and the impulse shaper OF can be applied (through an optocoupler OC) to the input of a rapid commutation shaper unit BFR.

The rapid commutation shaper unit BFR can have a reversal stage followed by a repeating stage. Each stage of the rapid commutation shaper unit can comprise a power commutation MOSFET with channel n, in which the gate protection circuit can include a p-n-p transistor. At the repeater output there can be positive impulses with very rapid drops, for example, with a drop of 3 ns, that can thereafter be applied to the input of the power amplifying unit AP. The power amplifying unit can have a final n-p-n transistor which can supply the high voltage step up transformer Tr. As a consequence of the transitory processes occurring in the transformer, in the high voltage secondary winding of the transformer there can be a damped oscillation which can comprise a negative impulse followed by a positive impulse. The secondary winding of the high voltage transformer can be connected to two rectifiers Ra and Rb of opposing charges. Each aforesaid rectifier can be followed by several serially-connected rectifying diodes. The first rectifier Ra can allow only the negative impulses to pass, while the second rectifier Rb can allow only the positive impulses to pass. The outputs of the two rectifiers can supply the two armatures of the electro-kinetic generator, wherein the output from the first rectifier Ra can be connected to the ion generators, while that of the second rectifier Rb can be connected to the neutralizing electrodes.

The optocoupler OC can control the impulses passing from the oscillating unit and the impulse shaper unit OF to the rapid commutation shaper unit BFR. The optocoupler can be activated by the control unit BC.

In one embodiment, the air sterilizer according to the present invention can function in three different working modes with different average air velocities. The first working mode can comprise an optocoupler which can be continuously activated, and as a consequence, the very high voltage generator can continuously generate and supply impulses to the electro-kinetic converter armatures. In the second working mode, the optocoupler can be activated intermittently, and a three second active period can alternate with a three second inactive period. During the inactive period, the passing of impulses through the optocoupler can be blocked. In the third working mode there can be an active period of three seconds followed by an inactive period of eighteen seconds. During each inactive period, impulses can be blocked by the optocoupler.

The control unit BC can comprise three push-button type switches which can allow the user to select and actuate a desired working condition. Thus, if, for example, the user selects the first working mode, the activation input N of the optocoupler OC can be ground connected. Such ground connection can result in the continuous activation of the optocoupler and the continuous passing of impulses to the power unit BP. On the other hand, if the second or third operating modes are selected by the user, the optocoupler activation input is ground connected through a second optocoupler, which can be intermittently activated by a suitable lagging signal. For the second working mode, the lagging signal can include a three second impulse followed by three second interval between impulses. If working mode three is selected, a three second impulse will be followed by an eighteen second interval. In any scenario, the respective lagging signal can be generated by a suitable signal generator.

Thus, the apparatus according to the present invention can be carried out in several ways, each of which can function in accordance with the working mode selected by the user.

In one embodiment of the apparatus according to the present invention, experimentation has yielded the following optimum dimensions for an electro-kinetic generator having 21 electro-kinetic cells and 40 needles for each cell. For the ion generator B, the needle diameter can be equal to 0.8 mm; the free space between the needles can be 0.8 mm, and the pitch $p_2$ can be 1.6 mm; the length of the points can be a minimum of 4 mm; the length of the support blade 6 can be 80 mm; the width of the support blade 6 can be 15 mm; and the thickness of the support blade 6 can be 0.7 mm. The width and thickness of the support blade 6 can be important for ensuring sufficient rigidity to the ion generator and, in the present invention, the minimum values have been selected to ensure such rigidity. For the profiled element that comprises the neutralizing electrode 5, the width of one side of the profiled element (the other side being equal) can be 7 mm; the length of the profiled element can be 82 mm; the free space between the two profiles can be 10 mm; and the angle between the profile wings can be 90 degrees.

In an embodiment with the dimensions and parameters in which the electro-kinetic generator comprises 21 cells, each cell having the dimensions presented above, and the generator operating in the first working mode where it continuously supplies impulses of about 9 kV, a minimum air velocity of 0.5 m/s can be obtained. This minimum air velocity corresponds to a handled volume of about 18 cm/h. In this working mode, this embodiment can be employed as an ozone generator.

A third working mode can be selected for use as an air sterilizer with negligible amounts (below a pre-established limit) of ozone generation. In this third working mode, the ionization occurs intermittently. In this construction, the air sterilizer is recommended to be installed in all enclosures with stale air because of the current activities carried out therein. For example, in public houses where smoking is permitted, in waiting halls, hospitals, work places containing noxious gasses, workshops where a large number of employees spend time, and anywhere productivity may be decreased because of the air quality. It can be seen that this apparatus, depending on various aforementioned factors, can be used in many working conditions.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

It is noted that the foregoing examples have been provided merely for the purpose of explanation and are in no way to be construed as limiting of the present invention. While the present invention has been described with reference to an exemplary embodiment, it is understood that the words, which have been used herein are words of description and illustration, rather than words of limitation. Changes may be made, within the purview of the appended claims, as presently stated and as amended without departing from the scope and spirit of the present invention in its aspects. Although the present invention has been described herein with reference to particular means, materials, and embodiments, the present invention is not intended to be limited to the particulars disclosed herein; rather, the present invention extends to all functionally equivalent structures, methods, and uses, such as are within the scope of the appended claims.

What is claimed is:

1. An air sterilizer comprising:
   an electro-kinetic converter having an ion generating electrode including:

at least one row of needles secured along at least one support plate, two or more lamellar plates, two or more U-shaped elastically deformable insulating covers, and a very high voltage power source, wherein the lamellar plates serve as neutralizing electrodes;

wherein the electro-kinetic converter comprises a rectangular frame having an upper plate, a lower plate, and two or more electrically insulating transverse plates, wherein the upper plate and the lower plate have margins;

wherein the upper plate and lower plate of the rectangular frame are joined at their ends by the electrically insulating transverse plates, there being a row of constant-pitch equally-spaced rectangular notches located on one of the margins of the upper plate or the lower plate;

wherein the ion generating electrode is introduced through the rectangular notches, two or more outward V-shaped openings which are interleaved and at the same pitch being located on a margin opposed to the ion generating electrode; and wherein the neutralizing electrodes are introduced through the V-shaped openings and are secured in place on the upper plate and the lower plate by the U-shaped elastically deformable insulating covers.

2. The air sterilizer according to claim 1, wherein the ion-generating electrode comprises a metal support blade and the at least one row of needles, wherein the at least one row of needles are fastened lengthwise and at a well-determined pitch along the metal support blade, the needles being parallel to one another and perpendicular to the metal support blade, and wherein the neutralizing electrodes are made of two or more elements of metal strip, profiled lengthwise in the shape of the letter V and having equal arms that open at an angle of from 60 degrees to 120 degrees.

3. The air sterilizer according to claim 2, wherein points of the at least one row of needles of the ion generating electrode are arranged along a straight line and parallel to each edge of the neutralizing electrodes and are equally-spaced therefrom.

4. The air sterilizer according to claim 2, wherein the very high voltage power source is a very high voltage impulse generator, which generates and applies consecutive negative and positive impulses between the upper plate and lower plate having the function of the electrodes, wherein the negative and positive impulses have a sufficiently high voltage so as to form an electric field in the region of points of the needles, and wherein the electric field is of a sufficient intensity to create an ionization process and a plasma zone.

5. The air sterilizer according to claim 1, wherein points of the at least one row of needles of the ion-generating electrode are arranged along a straight line and parallel to each edge of the neutralizing electrodes and are equally-spaced therefrom.

6. The air sterilizer according to claim 5, wherein the needles are made out of wire comprising stainless steel alloyed with titanium, and the needles have a diameter equal of 0.8 mm to 1.0 mm and a length of 10 mm to 15 mm, and the points of the needles are sharpened so that a ratio of the lengths of the points to the diameter of the needles is 5 to 10, and wherein minimum values of the ratio are selected based on supplying the converter with a lower voltage of 10 kV and maximum values for voltage higher than 10 kV, and the needles are spaced at a pitch equal to 1 mm to 5 mm on a support blade.

7. The air sterilizer according to claim 5, wherein the very high voltage power source is a very high voltage impulse generator, which generates and applies consecutive negative and positive impulses between the upper plate and lower plate having the function of the electrodes, wherein the negative and positive impulses have a sufficiently high voltage so as to form an electric field in the region of the points of the needles, and wherein the electric field is of a sufficient intensity to create an ionization process and a plasma zone.

8. The air sterilizer according to claim 7, further comprising an oscillating and impulse shaper unit comprises at least one of, an oscillator with an operational amplifier, an oscillator output signal, or an oscillator input shaper, wherein the oscillator with the operational amplifier generates saw-tooth waveforms and the frequency and the duration of ramps and drops of the saw-tooth waveforms are adjustable using a potentiometer, wherein the oscillator output signal is connected to, and processed by, the oscillator input shaper, and wherein the oscillator input shaper comprises six serially-connected logic reversers, which generate rectangular impulses with an adjustable pulse duty factor.

9. The air sterilizer according to claim 1, wherein the needles are made out of wire comprising stainless steel alloyed with titanium, and the needles have a diameter of 0.8 mm to 1.0 mm and a length of 10 mm to 15 mm, and points of the needles are sharpened so that a ratio of the lengths of the points to the diameter of the needles is 5 to 10, and wherein minimum values of the ratio are selected based on supplying the converter with a lower voltage of 10 kV and maximum values for voltage higher than 10 kV, and that the needles are spaced at a pitch equal to from 1 mm to 5 mm on a support blade.

10. The air sterilizer according to claim 9, wherein the very high voltage power source is a very high voltage impulse generator, which generates and applies consecutive negative and positive impulses between the upper plate and lower plate having the function of the electrodes, wherein the negative and positive impulses have a sufficiently high voltage so as to form an electric field in the region of the points of the needles, and wherein the electric field is of a sufficient intensity to create an ionization process and a plasma zone.

11. The air sterilizer according to claim 1, wherein the very high voltage power source is a very high voltage impulse generator which generates and applies consecutive negative and positive impulses between the upper plate and lower plate having the function of the electrodes, wherein the negative and positive impulses have a sufficiently high voltage so as to form an electric field in the region of points of the needles, and wherein the electric field is of a sufficient intensity to create an ionization process and a plasma zone.

12. The air sterilizer according to claim 11, wherein the very high voltage impulse generator comprises a network filter and an AC/DC frequency converter, wherein the AC/DC frequency converter supplies stabilized DC voltages, wherein the stabilized DC voltages provide power to functional units of the generator, and the functional units of the generator comprise at least one of, a control unit, an oscillating and impulse shaper unit, a rapid commutation shaper unit, or a power amplifier, and wherein the power amplifier supplies a voltage step up whose secondary winding is connected to two rectifiers supplying the upper plate and lower plate of the electro-kinetic converter.

13. The air sterilizer according to claim 12, wherein the rapid commutation shaper unit receives impulses generated by the oscillating and impulse shaper unit through an optocoupler, wherein the optocoupler comprises at least one of, a reverser unit or a repeating unit, wherein the reverser unit and the repeating unit comprise power commutation transistors at an output of the rapid commutation shaper unit, resulting in positive rectangular impulses with very rapid drops, wherein the very rapid drops are applied to an input of a power amplifier unit, and wherein the power amplifier unit supplies a voltage step up.

14. The air sterilizer according to claim 12, wherein impulses resulting in the secondary winding of a transformer comprise a negative impulse followed by a positive impulse for each positive impulse applied to an input of a power amplifying unit, wherein the positive impulse and the negative impulse are rectified by a first rectifier and a second rectifier, wherein the first rectifier and second rectifier comprise at least two serially-connected rectifying diodes, wherein the first rectifier allows only negative impulses to supply the ion generating electrode, and wherein the second rectifier allows only positive impulses to supply the neutralizing electrodes.

15. The air sterilizer according to claim 12, wherein impulses resulting in a secondary winding of a transformer comprise a negative impulse followed by a positive impulse for each positive impulse applied to an input of a power amplifying unit, wherein the positive impulse and the negative impulse are rectified by a first rectifier and a second rectifier, wherein the first rectifier and second rectifier comprise at least two serially connected rectifying diodes, wherein the first rectifier allows only negative impulses to supply the ion generating electrode, and wherein the second rectifier allows only positive impulses to supply the neutralizing electrodes.

16. The air sterilizer according to claim 1, further comprising an optocoupler controlling passing of impulses from an oscillating shaping unit to a rapid commutation shaper unit, wherein the optocoupler is controlled by signals transmitted by a control unit to allow a working mode to be selected from three possible working modes, wherein a lagging signal generator generates a corresponding lagging signal for each working mode, wherein the three possible working modes have a predefined duration in which the optocoupler is activated and a predefined duration in which it is deactivated, and wherein the control unit has a push button interface to allow a user to select one of the three possible working modes.

17. An air sterilizer comprising:

an electro-kinetic converter having a plurality of lamellar plates serving as neutralizing electrodes;

a rectangular frame having an upper plate and a lower plate, wherein the upper and lower plates are connected to the neutralizing electrodes;

an ion-generating electrode comprising a plurality of rows of needles secured with a well-determined pitch on a metal support blade connecting the upper and the lower plates, wherein the needles are parallel to one another and perpendicular to the metal support blade;

two U-shaped elastically deformable insulating covers covering the upper and the lower plates respectively;

two electrically insulating transverse plates connected to the rectangular frame;

a very high voltage power source having two conductors;

a first optocoupler controlling passing of impulses from an oscillating shaping unit to a rapid commutation shaper unit;

a lagging signal generator generating a corresponding lagging signal for each working mode, wherein the ion-generating electrode is introduced through rectangular notches, two or more outward V-shaped openings which are interleaved and are located at the same well-determined pitch on a margin opposed to the ion-generating electrode, wherein the neutralizing electrodes are made of two or more elements of metal strip, and have equal arms that open at an angle of from 60 degrees to 120 degrees, wherein points of the rows of needles are arranged along a straight line and parallel to each edge of the neutralizing electrodes and are equally-spaced therefrom, wherein the needles are made out of wire comprising stainless steel alloyed with titanium, and the needles have a diameter of 0.8 mm to 1.0 mm and a length of 10 mm to 15 mm, and the points of the needles are sharpened so that a ratio of the lengths of the points to the diameter of the needles is 5 to 10, and the needles are spaced at a pitch equal to from 1 mm to 5 mm on the metal support blade, wherein minimum values of the ratio are selected based on supplying the electro-kinetic converter with a lower voltage of 10 kV and maximum values for voltage higher than 10 kV, wherein the very high voltage power source is a very high voltage impulse generator having a network filter and an AC/DC frequency converter, which generates and applies consecutive negative and positive impulses between the upper plate and the lower plate having the function of the neutralizing electrodes, wherein the negative and positive impulses have a sufficiently high voltage so as to form an electric field, which is of sufficient intensity to create an ionization process and a plasma zone, in the region of the points of the needles, wherein the AC/DC frequency converter supplies stabilized DC voltages so as to provide power to functional units of the very high impulse generator, wherein the functional units comprise a control unit, an oscillating and impulse shaper unit, a rapid commutation shaper unit, and a power amplifier which supplies a voltage step up, wherein the power amplifier supplies the voltage step up whose secondary winding is connected to two rectifiers supplying the upper plate and the lower plate of the electro-kinetic converter, wherein the AC/DC frequency converter together with the network filter carry out a separation of nulls by creating a virtual null, which is different from a null of a supply network, for the other functional units of the high voltage impulse generator, wherein the oscillating and impulse shaper unit comprises an oscillator with an operational amplifier, an oscillator output signal, which is connected to, and processed by, an oscillator input shaper which has six serially-connected logic reversers, which generate rectangular impulses with an adjustable pulse duty factor, wherein the oscillator with the operational amplifier generates saw-tooth waveforms, and the frequency and the duration of ramps and drops of the saw-tooth waveforms are adjustable using a potentiometer, wherein the rapid commutation shaper unit receives impulses generated by the oscillating and impulse shaper unit through a second optocoupler comprising a reverser unit and a repeating unit, wherein the reverser unit and the repeating unit comprise power commutation transistors at an output of the rapid commutation shaper unit, resulting in positive rectangular impulses with very rapid drops which are applied to an input of a power amplifier unit, and wherein impulses resulting in a secondary winding of a transformer comprise a negative impulse followed by a positive impulse for each positive impulse applied to the input of the power amplifying unit, and wherein the positive impulse and the negative impulse are rectified by a first rectifier allowing only negative impulses to be supplied to the ion-generating electrode and a second rectifier allowing only positive impulses to be supplied to the neutralizing electrodes, both of which comprise at least two serially connected diodes.

* * * * *